United States Patent
Sasaki et al.

(10) Patent No.: US 12,051,193 B2
(45) Date of Patent: Jul. 30, 2024

(54) MEDICAL INFORMATION PROCESSING APPARATUS, SYSTEM, AND X-RAY DIAGNOSIS APPARATUS

(71) Applicant: CANON MEDICAL SYSTEMS CORPORATION, Otawara (JP)

(72) Inventors: Sho Sasaki, Utsunomiya (JP); Ryoichi Nagae, Nasushiobara (JP); Shingo Abe, Nasushiobara (JP); Hisato Takemoto, Nasushiobara (JP); Takuya Sakaguchi, Utsunomiya (JP); Fumimasa Shige, Otawara (JP); Tomoki Fujito, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 308 days.

(21) Appl. No.: 17/084,931

(22) Filed: Oct. 30, 2020

(65) Prior Publication Data
US 2021/0133969 A1 May 6, 2021

(30) Foreign Application Priority Data

Nov. 5, 2019 (JP) ................. 2019-200793
Oct. 29, 2020 (JP) ................. 2020-181588

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0077* (2013.01); *A61B 5/7267* (2013.01); *A61B 5/7275* (2013.01); *A61B 5/746* (2013.01); *A61B 6/00* (2013.01); *G06T 7/20* (2013.01); *G16H 30/40* (2018.01); *G16H 50/20* (2018.01); *G06T 2207/10016* (2013.01); *G06T 2207/10116* (2013.01); *G06T 2207/20081* (2013.01); *G06T 2207/30196* (2013.01)

(58) Field of Classification Search
None
See application file for complete search history.

(56) References Cited

U.S. PATENT DOCUMENTS 11,007,612 B2 * 5/2021 Chuang ................ B23B 31/302
11,200,427 B2 * 12/2021 Periaswamy .......... G06V 20/52
(Continued)

*Primary Examiner* — Nancy Bitar
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry is configured to obtain an image capturing a space in which a manipulation is being performed on an examined subject and non-image information related to at least one of the manipulation, the examined subject, or the space. Also, the processing circuitry is configured to detect a situation having a high possibility for an occurrence of an abnormality in the space, on the basis of the obtained image, the obtained non-image information, and first correspondence information. The first correspondence information indicates a correspondence relationship between two or more images capturing the space, non-image information, and abnormalities having a high possibility of occurring in the space.

18 Claims, 5 Drawing Sheets

(51) Int. Cl.
    *A61B 6/00*         (2024.01)
    *G06T 7/20*         (2017.01)
    *G16H 30/40*      (2018.01)
    *G16H 50/20*      (2018.01)

(56) References Cited

U.S. PATENT DOCUMENTS

| | | |
|---|---|---|
| 2009/0003521 A1 | 1/2009 | Camus et al. |
| 2014/0114308 A1 | 4/2014 | Tolkowsky et al. |
| 2017/0181720 A1 | 8/2017 | Akiyama et al. |
| 2019/0050987 A1* | 2/2019 | Hsieh ..................... G16H 30/40 |
| 2019/0150857 A1* | 5/2019 | Nye ........................ A61B 6/037 |
| 2020/0268472 A1* | 8/2020 | Wolf ...................... A61B 17/00 |
| 2021/0307621 A1* | 10/2021 | Svenson ............ A61B 5/02416 |

\* cited by examiner

MEDICAL INFORMATION PROCESSING APPARATUS, SYSTEM, AND X-RAY DIAGNOSIS APPARATUS

CROSS-REFERENCE TO RELATED APPLICATIONS

This application is based upon and claims the benefit of priority from Japanese Patent Application No. 2019-200793, filed on Nov. 5, 2019; and Japanese Patent Application No. 2020-181588, filed on Oct. 29, 2020; the entire contents of all of which are incorporated herein by reference.

FIELD

Embodiments described herein relate generally to a medical information processing apparatus, a system, and an X-ray diagnosis apparatus.

BACKGROUND

Conventionally, in medical examination rooms (hereinafter, "examination rooms") where a diagnosis process or treatment is performed on an examined subject, a plurality of medical staff members work while using various types of medical devices. For such examination rooms, a technique is known by which situations can be avoided where an X-ray diagnosis apparatus configured to image an examined subject comes into contact with the examined subject or a practitioner. In examination rooms, however, various types of abnormalities may occur besides an X-ray diagnosis apparatus coming into contact with an examined subject or a practitioner. It is sometimes difficult to predict the occurrence of such abnormalities in advance.

DETAILED DESCRIPTION

Exemplary embodiments of a medical information processing apparatus, a system, and an X-ray diagnosis apparatus will be explained in detail below, with reference to the accompanying drawings.

First Embodiment

A medical information processing apparatus according to an embodiment includes processing circuitry. The processing circuitry is configured to obtain an image capturing a space in which a manipulation is being performed on an examined subject and non-image information related to at least one of the manipulation, the examined subject, or the space. The processing circuitry is configured to detect a situation having a high possibility for an occurrence of an abnormality in the space, on the basis of the obtained image, the obtained non-image information, and first correspondence information. The first correspondence information indicates a correspondence relationship between image capturing the space, non-image information, and abnormalities having a high possibility of occurring in the space.

Figure 1:
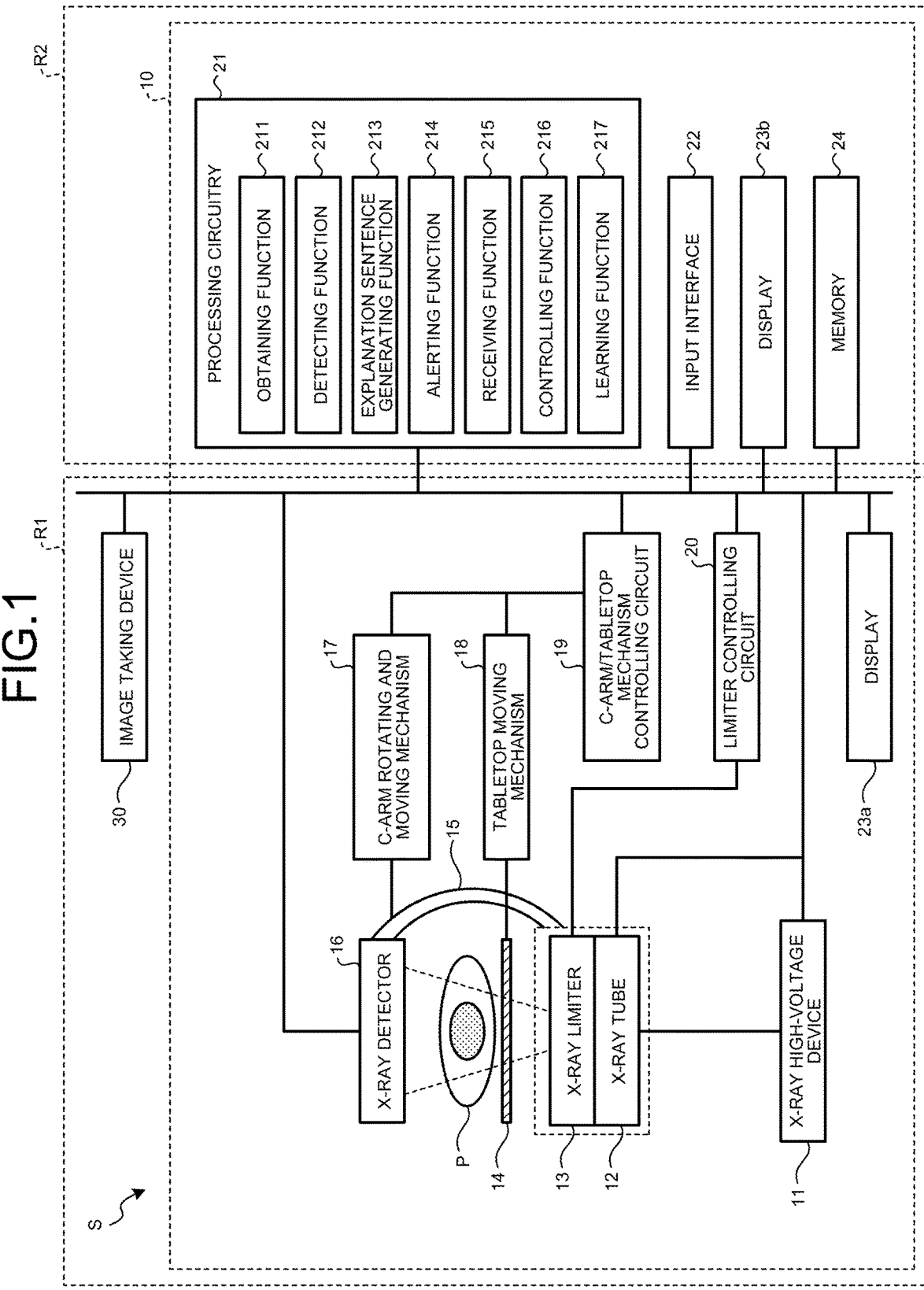
FIG. 1 is a block diagram illustrating an exemplary configuration of a system according to a first embodiment.

FIG. 1 is a block diagram illustrating an exemplary configuration of a system S according to the present embodiment. As illustrated in FIG. 1, the system S includes an X-ray diagnosis apparatus 10 and an image taking device 30.

The X-ray diagnosis apparatus 10 includes an X-ray high-voltage device 11, an X-ray tube 12, an X-ray limiter 13, a tabletop 14, a C-arm 15, an X-ray detector 16, a C-arm rotating and moving mechanism 17, a tabletop moving mechanism 18, a C-arm/tabletop mechanism controlling circuit 19, a limiter controlling circuit 20, processing circuitry 21, an input interface 22, displays 23a and 23b, and a memory 24. For example, the X-ray diagnosis apparatus 10 is an X-ray angiography apparatus. Further, in the present embodiment, the X-ray diagnosis apparatus 10 is an example of the medical information processing apparatus.

Of the constituent elements of the X-ray diagnosis apparatus 10, the X-ray high-voltage device 11, the X-ray tube 12, the X-ray limiter 13, the tabletop 14, the C-arm 15, the X-ray detector 16, the C-arm rotating and moving mechanism 17, the tabletop moving mechanism 18, the C-arm/tabletop mechanism controlling circuit 19, the limiter controlling circuit 20, and the display 23b are provided in an examination room R1.

Further, of the constituent elements of the X-ray diagnosis apparatus 10, the processing circuitry 21, the input interface 22, the display 23a, and the memory 24 are provided in a control room R2, for example.

The examination room R1 is a room in which a manipulation is performed on an examined subject (hereinafter, "patient") P. For instance, in the present embodiment, as an example of the manipulation, catheter treatment is implemented by practitioners on the patient P. Accordingly, the examination room R1 may be referred to as a catheter room. In the examination room R1, the practitioners represented by medical doctors and a plurality of other medical staff members work. The examination room R1 is an example of a space in which the manipulation is performed on the patient P in the present embodiment. The medical staff members include not only one or more medical doctors, but also one or more nurses and/or medical technologists. In the present embodiment, the practitioners and the other medical staff will collectively be referred to as medical providers.

Further, the control room R2 is, for example, a separate room positioned adjacent to the examination room R1. In the control room R2, an operator such as a medical technologist, a supervisor, or the like operates the input interface 22 or references the display 23a. Alternatively, another arrangement is also acceptable in which all the constituent elements of the X-ray diagnosis apparatus 10 are provided in the examination room R1.

The image taking device 30 is configured to image the inside of the examination room R1 and to transmit captured images to the X-ray diagnosis apparatus 10. In the present embodiment, the image taking device 30 is configured to take a video. The video taken by the image taking device 30 of the inside of the examination room R1 will be referred to as an examination room video (or examination room image).

Figure 2:
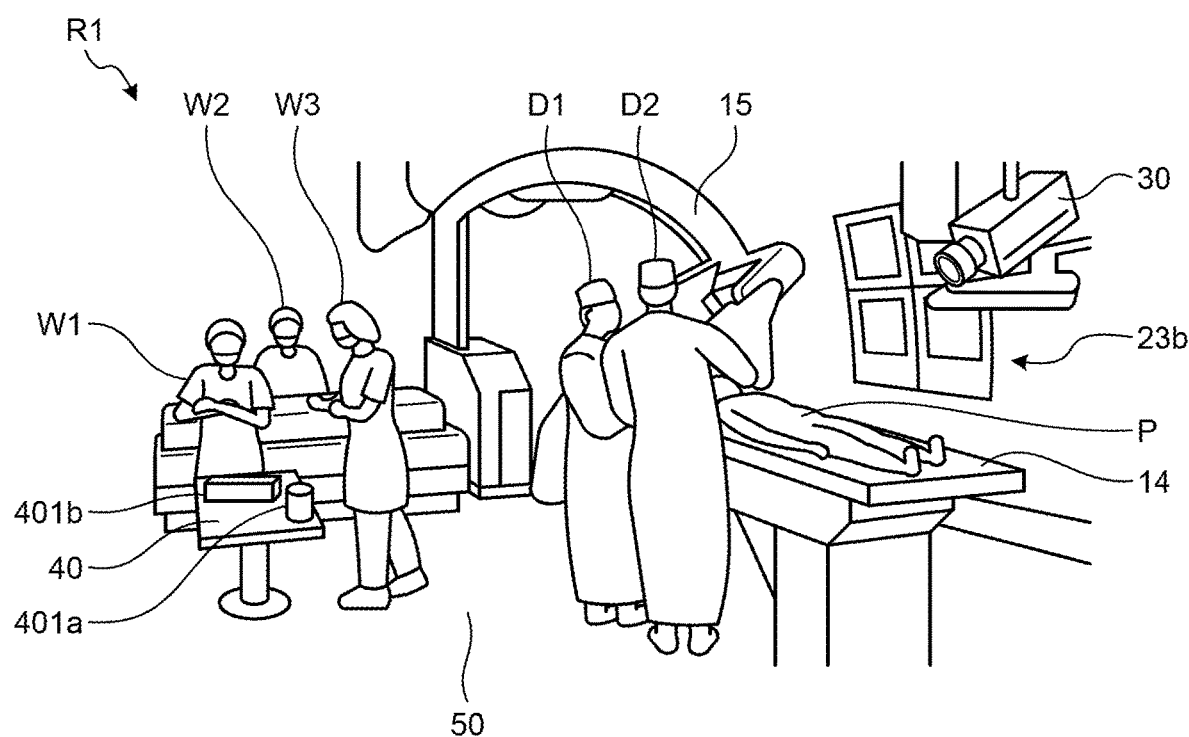
FIG. 2 is a drawing illustrating an example of an examination room according to the first embodiment.

FIG. 2 is a drawing illustrating an example of the examination room R1 according to the present embodiment. As illustrated in FIG. 2, the image taking device 30 is, for example, installed on the ceiling of the examination room R1. For example, the image taking device 30 is configured to image: the tabletop 14 on which the patient P is placed, the C-arm 15, practitioners D1 and D2 (hereinafter, simply "practitioners D") who perform the manipulation on the patient P all of which are in the examination room R1, as well as a plurality of medical staff members W1, W2, and W3 (hereinafter, simply "medical staff W") who work in the examination room R1, a floor 50 of the examination room R1, various types of devices and a medical table 40 provided in the examination room R1, medical tools 401a and 401b (which hereinafter will simply be referred to as "medical tools 401" when not being distinguished from each other) on the medical table 40, and the like.

Although FIGS. 1 and 2 illustrate the one image taking device 30, the number of image taking devices 30 is not particularly limited. Two or more images taking devices 30 may be provided.

Returning to the description of FIG. 1, the X-ray high-voltage device 11 is a high-voltage power source configured to generate high voltage and to supply the generated high voltage to the X-ray tube 12 under control of the processing circuitry 21.

The X-ray tube 12 is configured to generate X-rays by using the high voltage supplied from the X-ray high-voltage device 11. The X-ray limiter 13 is configured, under the control of the limiter controlling circuit 20, to limit the X-rays generated by the X-ray tube 12, so as to be selectively radiated onto a Region Of Interest (ROI) of the patient P.

The tabletop 14 is a bed on which the patient P is placed and is arranged over a table device (not illustrated). In this situation, the table device (not illustrated) may be included in the X-ray diagnosis apparatus 10 or may be provided outside the X-ray diagnosis apparatus 10. Even when not being included in the X-ray diagnosis apparatus 10, the table device may be included in the system S. The patient P is not included in the X-ray diagnosis apparatus 10.

The X-ray detector 16 is configured to detect X-rays that have passed through the patient P and to transmit a detection result to the processing circuitry 21.

The C-arm 15 is configured to hold the X-ray tube 12, the X-ray limiter 13, and the X-ray detector 16. The C-arm rotating and moving mechanism 17 is a mechanism configured to rotate and move the C-arm 15, by driving a motor or the like provided for a supporting unit. The tabletop moving mechanism 18 is a mechanism configured to move the tabletop 14. For example, the tabletop moving mechanism 18 is configured to move the tabletop 14 by using motive power generated by an actuator.

Under the control of the processing circuitry 21, the C-arm/tabletop mechanism controlling circuit 19 is configured to adjust the rotation and the moving of the C-arm 15 and the moving of the tabletop 14, by controlling the C-arm rotating and moving mechanism 17 and the tabletop moving mechanism 18. Under the control of the processing circuitry 21, the limiter controlling circuit 20 is configured to control the radiation range of the X-rays radiated onto the patient P, by adjusting opening degrees of limiting blades included in the X-ray limiter 13.

The input interface 22 is realized by using a trackball, a switch button, a mouse, a keyboard, a touch pad, and/or the like, as well as a foot switch or the like for causing the X-rays to be radiated. The input interface 22 is connected to the processing circuitry 21 and is configured to convert input operations received from the operator into electrical signals and to output the electrical signals to the processing circuitry 21.

Each of the displays 23a and 23b is configured to display a GUI (Graphical User Interface) used for receiving instructions from the operator and setting values of the X-ray diagnosis apparatus 10, various types of images generated by the processing circuitry 2', and the like. For example, in the present embodiment, each of the displays 23a and 23b is configured to display risk alert image presenting a risk for the occurrence of abnormalities detected by a detecting function 212 (explained later).

More specifically, for example, the display 23a is installed as being hung from the ceiling of the examination room R1. The number of screens of the display 23a does not necessarily have to be one and may be two or more. The display 23a may be referred to as an examination-room display.

Further, the display 23b is provided in the control room R2. The display 23b may be referred to as a control-room display. The number of displays 23b is not particularly limited. One display 23b or two or more displays 23b may be provided. In the following sections, when not being particularly distinguished from each other, the display devices 23a and 23b may simply be referred to as display devices 23.

In the present embodiment, examples of the abnormalities that may occur in the examination room R1 include: one of the medical tools 401 falling; one of the medical devices coming into contact with the patient P or any of the medical providers; the medical tools 401 to be used for the manipulation not being sufficiently prepared; a medical provider falling; and disinfected locations becoming contaminated.

Further, examples of the situation where one of the medical devices comes into contact with the patient P or a medical provider include: the C-arm 15 or the tabletop 14 coming into contact with another medical device, the patient, or a medical provider; a medical provider coming into contact with a medical device other than the X-ray diagnosis apparatus 10; and medical providers coming into contact with each other.

The situation in which the medical tools 401 to be used for the manipulation are not sufficiently prepared denotes a situation where the medical tools 401 have not been arranged in predetermined expected positions prior to the start of the manipulation.

The fall of a medical provider denotes, for example, situations where the medical provider falls or loses his/her balance when almost falling down, by tripping on cables running all over the floor of the examination room R1.

The situation where the disinfected locations become contaminated denotes, for example, an undisinfected object, a medical provider, or the like coming into contact with any of the disinfected locations.

The descriptions above are merely examples. Possible abnormalities that may occur in the examination room R1 are not limited to these examples.

Further, in the X-ray diagnosis apparatus 10, processing functions are stored in the memory 24 in the form of computer-executable programs. The C-arm/tabletop mechanism controlling circuit 19, the limiter controlling circuit 20, and the processing circuitry 21 are processors configured to realize the functions corresponding to the programs, by reading and executing the programs from the memory 24. In other words, the circuits that have read the programs have the functions corresponding to the read programs.

The memory 24 has stored therein the programs that correspond to the various types of functions and are read and executed by the circuits illustrated in FIG. 1. For example, the memory 24 is realized by using a semiconductor memory element such as a Random Access Memory (RAM), a flash memory, or the like, or a hard disk, an optical disk, or the like. The memory 24 is an example of a storage unit.

The processing circuitry 21 includes an obtaining function 211, the detecting function 212, an explanation sentence generating function 213, an alerting function 214, a receiving function 215, a controlling function 216, and a learning function 217. The obtaining function 211 is an example of an obtaining unit. The detecting function 212 is an example of a detecting unit. The explanation sentence generating function 213 is an example of an explanation sentence generating unit. The alerting function 214 is an example of an alerting unit. The receiving function 215 is an example of a receiving unit. The controlling function 216 is an example of a controlling unit. The learning function 217 is an example of a learning unit.

Although FIG. 1 illustrates the example in which the single piece of processing circuitry (i.e., the processing circuitry 21) realizes the processing functions, namely, the obtaining function 211, the detecting function 212, the explanation sentence generating function 213, the alerting function 214, the receiving function 215, the controlling function 216, and the learning function 217, it is also acceptable to structure the processing circuitry 21 by combining together a plurality of independent processors, so that the processing functions are realized as a result of the processors executing the programs.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the memory 24, it is also acceptable to directly incorporate the programs in the circuits of one or more processors. In that situation, the one or more processors realize the functions by reading and executing the programs incorporated in the circuits thereof.

The obtaining function 211 is configured to obtain one or more images capturing the examination room R1 where the manipulation is being performed on the patient. The obtaining function 211 is configured to obtain at least one image. More specifically, the obtaining function 211 according to the present embodiment is configured to obtain an examination room video capturing the inside of the examination room R1, from the image taking device 30.

Further, the obtaining function 211 is configured obtain non-image data related to at least one of the manipulation, the patient P, and the examination room R1.

For example, the non-image data includes at least one of the following: manipulation information related to the manipulation; patient information related to the patient P; practitioner information related to the practitioners D who perform the manipulation; device information related to the devices used for the manipulation; and medical institution information related to the medical institution where the examination room R1 is provided. The non-image data is an example of the non-image information of the present embodiment.

For example, the manipulation information may indicate the type of the manipulation. The type of the manipulation is, more specifically, the type of a protocol or a program executed by the X-ray diagnosis apparatus 10 at the time of performing the manipulation. For example, the protocol is a processing procedure determined for each treated site. The program is represented by processes executed in each protocol and may be, for example, a program that executes scan steps of Digital Subtraction Angiography (DSA) or the like.

Further, the manipulation information may be information related to the time of the day when the manipulation is performed. For example, the time of the day when the manipulation is performed may be the manipulation start time or may be one of the time span categories such as "morning", "daytime" and "late night" in which the manipulation start time is included. For example, manipulations performed late at night are often emergency treatment and may exhibit a regular pattern, in some situations, where there is a higher possibility for the occurrence of an abnormality than manipulations performed in the morning or daytime.

Further, the manipulation information may be information indicating the day of the week on which the manipulation is performed. For example, some medical institutions may have a regular pattern in the scheduling based on days of the week, such as treating patients P having serious symptoms in the first half of the week, and implementing treatment or performing less difficult medical examinations on patients P having minor symptoms in the second half of the week.

Further, the manipulation information may be information indicating the degree of difficulty of the manipulation.

The patient information is, for example, information about the degree of seriousness of the medical condition of the patient P, the age of the patient P, the gender of the patient P, and/or the like.

The practitioner information is, for example, information indicating the degrees of proficiency of the practitioners D. For example, the practitioner information may indicate one of the categories corresponding to degrees of proficiency such as "inexperienced", "experienced", and "a medical instructor". Alternatively, the practitioner information may indicate the degrees of proficiency of the practitioners D by using numerical values. Possible examples of the practitioner information are not limited to these examples. The practitioner information may include various types of information other than the degrees of proficiency.

The device used for the manipulation is, for example, the X-ray diagnosis apparatus 10. In other words, the device information related to the devices used for the manipulation is, for example, device information related to the X-ray diagnosis apparatus 10. The device information related to the X-ray diagnosis apparatus 10 is, for example, position information of movable mechanisms included in the X-ray diagnosis apparatus 10. The movable mechanisms include at least either the C-arm 15 or the tabletop 14. The movable mechanisms may include both the C-arm 15 and the tabletop 14. For example, the obtaining function 211 is configured to obtain the position information of the C-arm 15 or the tabletop 14 from the C-arm/tabletop mechanism controlling circuit 19. The device information may be referred to as machine information.

Further, the device information may be information related to any of the other devices used for the manipulation. The information related to the other devices used for the manipulation is, for example, the number of catheters or the types of the catheters used for the manipulation. Possible examples of the other devices are not limited to the catheters and may be a balloon, a stent, or the like. When different devices are used for the manipulation, different devices need to be prepared.

The medical institution information is, for example, information indicating the region where the medical institution having the examination room R1 is located. The region where the medical institution having the examination room R1 is located, i.e., the region where the medical institution having the X-ray diagnosis apparatus 10 is located is, for example, the prefecture in which the medical institution is located. When insurance systems vary among regions, the type of the manipulation and the types and/or the quantity of the devices used for the manipulation also vary.

The non-image data described above may be obtained from any of the other constituent elements of the X-ray diagnosis apparatus 10 or from an external device. For example, the obtaining function 211 may be configured to obtain the non-image data input by the operator via an input interface. Alternatively, the obtaining function 211 may be configured to obtain the patient information about the patient P or the region in which the medical institution having the examination room R1 is located, from an electronic medical record system.

The obtaining function 211 is configured to send the obtained examination room video and non-image data to the detecting function 212.

On the basis of the obtained image, the detecting function 212 is configured to detect a situation having a high possibility for the occurrence of an abnormality in the examination room R1. More specifically, the detecting function 212 is configured to detect a risk region in the examination room video, on the basis of the examination room video and the non-image data obtained by the detecting function 212 and a first trained model.

The first trained model is configured to indicate a correspondence relationship between a plurality of examination room videos capturing the examination room R1 and abnormalities having a high possibility of occurring in the examination room R1. More specifically, the first trained model according to the present embodiment is configured to indicate the correspondence relationship among the plurality of examination room videos capturing the examination room R1, the non-image data, and the abnormalities having a high possibility of occurring in the examination room R1. The first trained model is an example of the first correspondence information of the present embodiment.

In the present embodiment, a first trained model 91 is generated by the learning function 217 (explained later) and saved in the memory 24. Further, the first trained model 91 is structured with a neural network and trained parameter data.

Further, the risk region is an image region having a high possibility for the occurrence of the abnormality in the examination room video. More specifically, the risk region is an image region rendering a situation immediately prior to the occurrence of the abnormality.

The "situation having a high possibility for the occurrence of an abnormality" is, for example, a situation having a probability for the occurrence of an abnormality equal to or higher than a threshold value. For instance, examples of the abnormality include "one of the medical tools 401 falling". Even if the examination room video itself does not render the medical tool falling, when one of the frames included in the examination room video renders a situation in which the possibility for a medical tool 401 to fall is equal to or higher than the threshold value, the first trained model 91 outputs, as the risk region, such an image region within the frame that renders the medical tool having the high possibility of falling.

Also, examples of the abnormality include "a medical provider falling". Even if no medical provider has fallen yet, when the examination room video renders a situation in which cables are running all over the floor 50, the first trained model 91 outputs, as the risk region, such an image region within the frame rendering the situation that renders the cables running all over. In some situations, two or more risk regions may be detected from a single frame.

Figure 3:
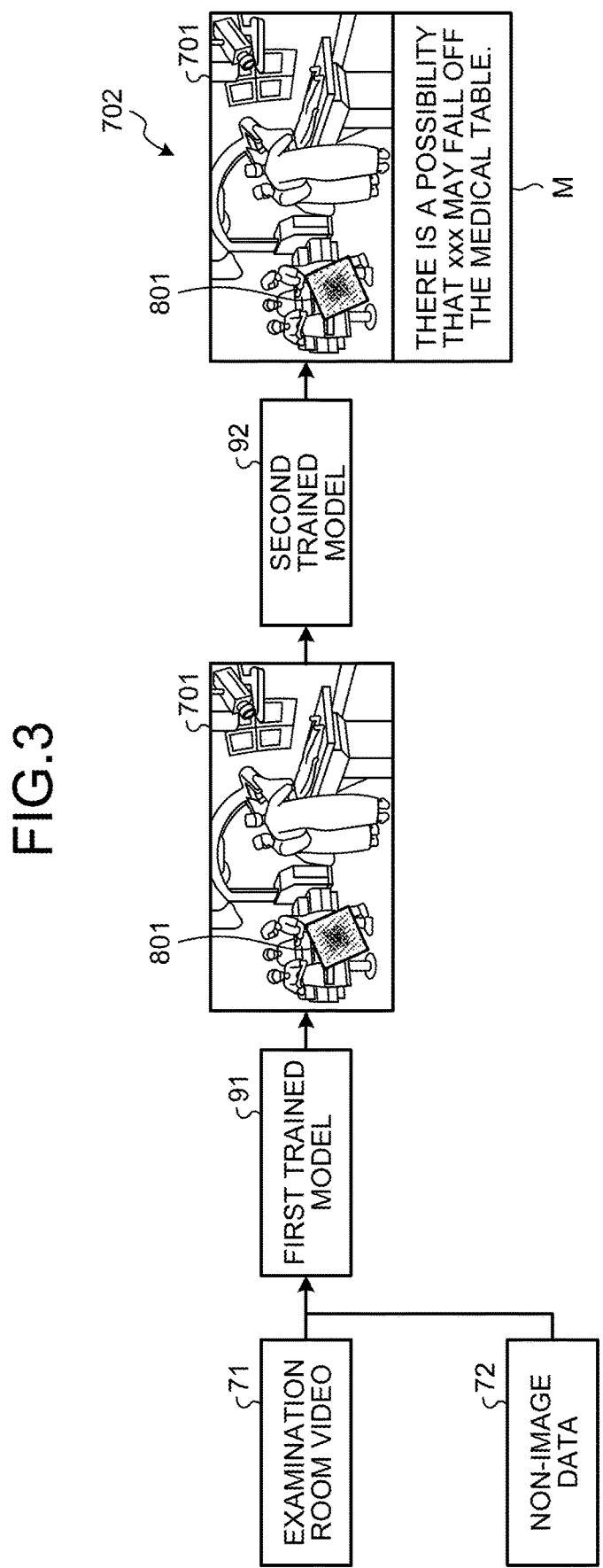
FIG. 3 is a chart illustrating examples of a risk detecting process and a risk alerting process on a risk for the occurrence of an abnormality according to the first embodiment.

FIG. 3 is a chart illustrating examples of a risk detecting process and a risk alerting process on a risk for the occurrence of an abnormality according to the present embodiment.

For example, the first trained model 91 is a trained model generated through deep learning of a neural network or the like. As a method for the deep learning, a Recurrent Neural Network (RNN), Long Short-Time Memory (LSTM), or the like may be used. Alternatively, the first trained model 91 may be generated through other types of deep learning or machine learning.

The detecting function 212 is configured to read the first trained model 91 from the memory 24 and, as illustrated in FIG. 3, to input an examination room video 71 and non-image data 72 to the first trained model 91.

On the basis of the examination room video 71 and the non-image data 72 having been input thereto, the first trained model 91 is configured to detect, from a plurality of frames included in the examination room video 71, one or more risk regions rendering a situation having a high possibility for the occurrence of an abnormality. When having detected that one of the plurality of frames included in the examination room video 71 renders the situation having a high possibility for the occurrence of an abnormality, the first trained model 91 generates one or more risk images 801 indicating the one or more risk regions within the frame rendering the situation having the high possibility for the occurrence of the abnormality.

In the present embodiment, by inputting the examination room video 71 to the first trained model 91, the detecting function 212 is configured to detect the situation having the high possibility for the occurrence of an abnormality according to one or both of a moving speed and a moving direction of one of the objects and the human beings rendered in the examination room video 71, on the basis of time-series relationships among the plurality of frames included in the examination room video 71.

For example, the first trained model 91 is configured to detect a rise in the possibilty for the occurrence of an abnormality, on the basis of moving directions or speeds of the medical devices or the medical providers rendered in the examination room video 71. In a specific example, while a practitioner D is moving toward the medical table 40 with his/her back facing the medical table 40, when the distance between the practitioner D and the medical table 40 becomes equal to or shorter than a prescribed distance, the first trained model 91 detects the occurrence of an abnormality where "the practitioner D comes into contact with the medical table 40". In another example, even when the distance between a practitioner D and the medical table 40 becomes equal to or shorter than the prescribed distance, if the practitioner D is facing the medical table 40, the first trained model 91 detects no occurrence of abnormalities. The present description of the abnormality detection is merely an example and is not intended to limit the abnormality detecting functions of the detecting function 212.

Further, in addition to the examination room video 71, the first trained model 91 is configured to detect the possibility for the occurrence of an abnormality on the basis of any of the following that was input as the non-image data 72: the manipulation information related to the manipulation, the patient information related to the patient P, the practitioner information related to the practitioners D who perform the manipulation; the device information related to the devices used for the manipulation; the medical institution information related to the medical institution where the examination room R1 is provided; and the like. For example, depending on the degrees of proficiency of the practitioners D and the time of the day when the manipulation is performed, the possibility for the occurrence of an abnormality may increase or decrease. The first trained model 91 is configured to detect a rise in the possibility for the occurrence of an abnormality, while taking into account the fluctuation in the possibility for the occurrence of an abnormality based on the non-image data 72.

Further, the device information included in the non-image data 72 includes the position information of the movable mechanisms provided in the X-ray diagnosis apparatus 10. Accordingly, the first trained model 91 is configured to detect the rise in the possibility for the occurrence of an abnormality, while taking into account fluctuation in the possibility for the occurrence of an abnormality based on the positions of the C-arm 15, the tabletop 14, and the like in blind spots of the image taking device 30 that are not rendered in the examination room video 71.

In the following sections, image including the risk image 801 generated by the detecting function 212 will be referred to as risk examination room image 701. In the present embodiment, the risk examination room image 701 is image in which the risk image 801 is superimposed on a frame included in the examination room video 71 that renders the situation having the high possibility for the occurrence of an abnormality.

As illustrated in FIG. 3, the risk image 801 is, for example, a heatmap expressing heights of possibility of the occurrence of abnormalities. As a method for generating the heatmap expressing the heights of the possibility of the occurrence of abnormalities, publicly-known techniques such as Gradient-weighted Class Activation Mapping (Grad-CAM) may be used. The display mode of the risk image 801 is not limited to the heatmap. A border enclosing the risk region may be displayed.

The detecting function 212 is configured to send the risk examination room image 701 including the risk image 801 having been generated, to the explanation sentence generating function 213.

Returning to the description of FIG. 1, on the basis of a second trained model, the explanation sentence generating function 213 is configured to generate a sentence explaining the abnormality having the high possibility of occurring in the risk region detected by the detecting function 212.

The second trained model indicates a correspondence relationship between a plurality of risk regions in the plurality of images capturing the examination room R1 and phrases explaining abnormalities having a high possibility of occurring in the plurality of risk regions. For example, a second trained model 92 is a model that has further learned, in addition to a correspondence relationship between objects rendered in examination room videos and the names of the objects, natural sentences describing "situations in which an abnormality is about to occur" rendered in risk regions included in the examination room videos. The second trained model is an example of the second correspondence information of the present embodiment.

More specifically, for example, the second trained model is a trained model generated through deep learning using an RNN, a Convolutional Neural Network (CNN), or the like and is configured to output the explanation sentence describing input image by using a sentence. Alternatively, the second trained model may be generated through other types of deep learning or machine learning. In the present embodiment, the second trained model is generated by the learning function 217 (explained later).

Next, the explanation sentence generating process performed by the second trained model 92 will be explained, with reference to FIG. 3 again. The explanation sentence generating function 213 is configured to read the second trained model 92 from the memory 24 and to input the risk examination room image 701 generated by the detecting function 212 to the second trained model 92.

The second trained model 92 is configured to perform an image recognition on the objects rendered in the risk examination room image 701 and to identify the names of the objects. The objects also include people. Examples of the objects rendered in the risk examination room image 701 include medical tools 401, the medical table 40, the C-arm 15, the tabletop 14, the practitioners D, the patient P, but are not limited to these. Further, as for the medical tools 401, the second trained model 92 is capable of individually recognizing the name of each of the various types of medical tools 401.

Further, the second trained model 92 is configured to output the explanation sentence explaining the "situation in which an abnormality is about to occur" rendered in the risk region presented in the risk image a 801 within the risk examination room image 701. In the explanation sentence, the second trained model 92 uses, as necessary, the names of the objects recognized from the risk examination room image 701.

In the example illustrated in FIG. 3, the second trained model 92 generates an explanation sentence M stating "there is a possibility that xxx may fall off the medical table". The symbol "xxx" in the explanation sentence M denotes the name of the medical tool 401 having the possibility of falling. The explanation sentence M in FIG. 3 is an example. Possible sentences explaining an abnormality having a high possibility of occurring in a risk region are not limited to this example.

The explanation sentence generating function 213 is configured to send alert image 702 obtained by adding the explanation sentence M to the risk examination room image 701, to the alerting function 214. The alert image 702 is image including the risk examination room image 701 containing the risk image 801 such as the heatmap and the explanation sentence M.

Returning to the description of FIG. 1, the alerting function 214 is configured to alert about a high possibility for the occurrence of an abnormality, when the detecting function 212 has detected that there is a high possibility for the occurrence of the abnormality. Further, the alerting function 214 is configured to output the explanation sentence M generated by the explanation sentence generating function 213. More specifically, the alerting function 214 causes the displays 23a and 23b to display the alert image 702 generated by the explanation sentence generating function 213. The alerting function 214 may cause both of the displays 23a and 23b to display the alert image 702 or may cause only one of the displays 23a and 23b to display the alert image 702.

For example, when the display 23a in the examination room R1 has a plurality of screens, but one of the screens is unused, the alerting function 214 is configured to display the alert image 702 on the unused screen of the display device 23a. Further, when a plurality of display devices 23b are provided in the control room R2, the alerting function 214 is configured to cause one of the display devices 23b displaying no other image to display the alert image 702.

In another example, when the display devices 23a and 23b have no vacant screens, the alerting function 214 is configured to replace one of the images being displayed with the alert image 702. In the present embodiment, the priority ranking of the information displayed on the display devices 23a and 23b is the highest for medical image and the second highest for the alert image 702. When the display devices 23a and 23b are displaying image having a lower priority (e.g., setting values of the X-ray diagnosis apparatus 10) than the alert image 702, the alerting function 214 terminates the display of the image having the lower priority and displays the alert image 702 instead. Possible display locations of the alert image 702 are not limited to the above example.

Further, the alerting function 214 may output the explanation sentence M via audio, by controlling a speaker (not illustrated) or the like. Further, the alert image 702 may output an alert sound together with the display of the alert image 702.

Further, when the receiving function 215 (explained later) has received an alert stop operation from the operator, the alerting function 214 is configured to stop the display of the alert image 702, the audio output of the explanation sentence M, or the output of the alert sound.

The receiving function 215 is configured to receive operations input by the operator, via the input interface 22. For example, the receiving function 215 is configured to receive the alert stop operation input by the operator. The receiving function 215 is configured to send information indicating the receipt of the alert stop operation, to the alerting function 214. Further, the receiving function 215 is also configured to receive an operation to start or end the image taking process of the X-ray diagnosis apparatus 10 input by the operator. Upon receipt of the operation to start or end the image taking process, the receiving function 215 is configured to send information indicating the receipt of the operation to start or end the image taking process, to the controlling function 216.

On the basis of the operation to start or end the image taking process received by the receiving function 215, the controlling function 216 is configured to perform the image taking process to image the patient P, by controlling the entirety of the X-ray diagnosis apparatus 10. For example, the controlling function 216 is configured to control the rotation and the moving of the C-arm 15 and the moving of the tabletop 14, by controlling the C-arm/tabletop mechanism controlling circuit 19. Further, the controlling function 216 is configured to control the radiation of the X-rays onto the patient P, by controlling the X-ray high-voltage device 11 and the limiter controlling circuit 20. Also, the controlling function 216 is configured to obtain an X-ray image on the basis of electrical signals converted from the X-rays by the X-ray detector 16.

The learning function 217 is configured to generate the first trained model 91, by learning a relationship between a plurality of abnormality pre-occurrence images and abnormality pre-occurrence image regions rendering locations of the occurrence of abnormality in the plurality of abnormality pre-occurrence images.

The abnormality pre-occurrence image is an image capturing the examination room R1 at a time prior to the occurrence of an abnormality during the manipulation.

Further, the learning function 217 is configured to further learn a relationship between the non-image data 72 related to the manipulation of which the abnormality pre-occurrence image was captured and the abnormality pre-occurrence image regions. Also, in addition to the abnormality pre-occurrence image, the learning function 217 may further learn relationships between an image capturing situations in which an abnormality has actually occurred as well as an image capturing situations in which no abnormalities have occurred and whether an abnormality has occurred or not.

Figure 4:
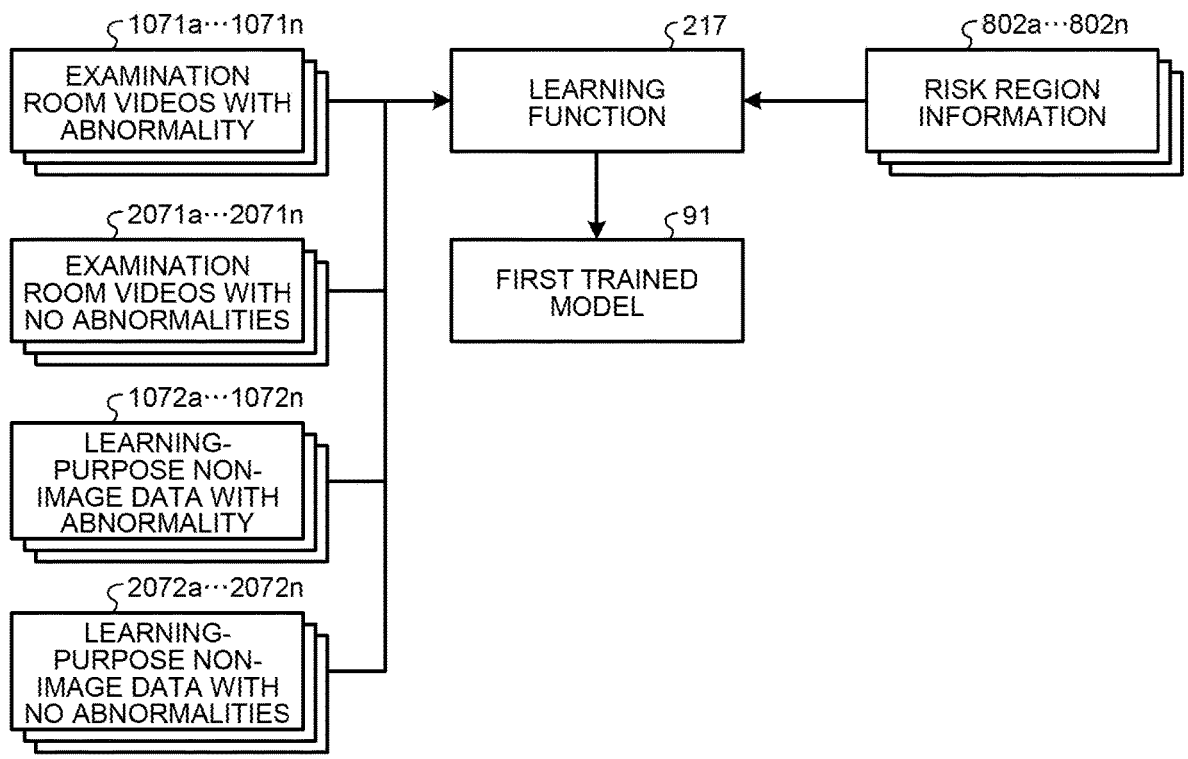
FIG. 4 is a chart illustrating an example of a method for generating a first trained model according to the first embodiment.

The process of generating the first trained model 91 according to the present embodiment will specifically be explained, with reference to FIG. 4. FIG. 4 is a chart illustrating an example of a method for generating the first trained model 91 according to the present embodiment. In the present embodiment, as illustrated in FIG. 4, the learning function 217 obtains, as learning data, a plurality of examination room videos with an abnormality 1071a to 1071n, a plurality of examination room videos with no abnormalities 2071a to 2071n, learning-purpose non-image data with an abnormality 1072a to 1072n, and learning-purpose non-image data with no abnormalities 2012a to 2072n. Further, the learning function 217 obtains, as training data, a plurality of risk regions information 802a to 802n.

Each of the plurality of examination room videos with an abnormality 1071a to 1071n is a video capturing a situation in which an abnormality has occurred during a manipulation in the examination room R1. In the following sections, when not being individually distinguished from one another, the examination room videos with an abnormality 1071a to 1071n may simply be referred to as examination room videos with an abnormality 1071.

Each of the plurality of examination room videos with no abnormalities 2071a to 2071n is a video capturing a situation in which no abnormalities have occurred during a manipulation in the examination room R1. In the following sections, when not being individually distinguished from one another, the examination room videos with no abnormalities 2071a to 2071n may simply be referred to as examination room videos with no abnormalities 2071.

The examination room videos with an abnormality 1071 and the examination room videos with no abnormalities 2071 may each be a video capturing the entire manipulation from the start to the end or may be a video capturing a partial time period during the manipulation. Further, the examination room videos with an abnormality 1071 and the examination room videos with no abnormalities 2071 may each be a video actually capturing the examination room R1 or may each be a video capturing another examination room. Further, the sources from which the examination room videos with an abnormality 1071 and the examination room videos with no abnormalities 2071 are obtained are not particularly limited. For example, the learning function 217 may obtain the examination room videos with an abnormality 1071 and the examination room videos with no abnormalities 2071 from an external device outside the system S or from the image taking device 30.

The learning-purpose non-image data with an abnormality 1072a to 1072n is non-image data corresponding to the plurality of examination room videos with an abnormality 1071a to 1071n, respectively. For example, the learning-purpose non-image data with an abnormality 1072a is kept in correspondence with the examination room video with an abnormality 1071a. In the following sections, when not being individually distinguished from one another, the learning-purpose non-image data with an abnormality 1072a to 1072n may simply be referred to as learning-purpose non-image data with an abnormality 1072.

The learning-purpose non-image data with no abnormalities 2072a to 2072n s non-image data corresponding to the examination room videos with no abnormalities 2071a to 2071n, respectively. In the following sections, when not being individually distinguished from one another, the learning-purpose non-image data with no abnormalities 2072a to 2072n may simply be referred to as learning-purpose non-image data with no abnormalities 2072.

Similarly to the non-image data 72, the learning-purpose non-image data with an abnormality 1072 and the learning-purpose non-image data with no abnormalities 2072 each includes at least one of the following: manipulation information related to the manipulation; patient information related to the patient P; practitioner information related to the practitioners D who perform the manipulation; device information related to the devices used for the manipulation; and medical institution information related to the medical institution where the examination room R1 is provided.

The risk region information 802a to 802n is training data for specifying a risk region in the plurality of examination room videos with an abnormality 1071a to 1071n, respectively. In the following sections, when not being individually distinguished from one another, the risk region information 802a to 802n may simply be referred to as risk region information 802.

More specifically, the risk region information 802 is information with which it is possible to identify the frame immediately preceding the frame rendering the abnormality included in the examination room video with an abnormality 1071 and a risk region in the frame immediately preceding the frame rendering the abnormality. The frame immediately preceding the frame rendering the abnormality is an example of the abnormality pre-occurrence image of the present embodiment.

Further, the risk region in the frame immediately preceding the frame rendering the abnormality is an example of the abnormality pre-occurrence image region of the present embodiment. The risk region in the frame immediately preceding the frame rendering the abnormality is, for example, an image region rendering a cause of the abnormality. More specifically, when the abnormality that has occurred is "one of the medical tools 401 falling", the image region rendering the medical tool 401 within the frame rendering the situation prior to the falling of the medical tool 401 is the risk region. In another example, when the abnormality that has occurred is "one of the medical devices coming into contact with a practitioner D", the image region rendering the medical device and the practitioner D within the frame rendering the situation immediately prior to the contact between the medical device and the practitioner D is the risk region.

The sources from which the risk region information 802, the learning-purpose non-image data with an abnormality 1072, and the learning-purpose non-image data with no abnormalities 2072 are obtained are not particularly limited. For example, the learning function 217 may obtain the risk region information 802, the learning-purpose non-image data with an abnormality 1072, and the learning-purpose non-image data with no abnormalities 2072 that are input by the operator or may obtain the risk region information 802, the learning-purpose non-image data with an abnormality 1072, and the learning-purpose non-image data with no abnormalities 2072 from an external device.

The learning function 217 is configured to generate the first trained model 91 by performing deep learning using a CNN, an RNN, or the like, on the basis of the learning data and the training data described above.

For example, in the present embodiment, on the basis of time-series relationships between the plurality of frames included in the examination room videos with an abnormality 1071 and the examination room videos with no abnormalities 2071, the learning function 27 is configured to learn the situations having a high possibility for the occurrence of an abnormality, according to one or both of the moving speed and the moving direction of one of the objects and the human beings rendered in the examination room videos with an abnormality 1071 and the examination room videos with no abnormalities 2071. For example, even when the distance between a practitioner D and the medical table 40 is the same in an examination room video with an abnormality 1071 and in an examination room video with no abnormalities 2071, the abnormality where "a practitioner D comes into contact with the medical table 40" may occur or may not occur, depending on the moving speed and the moving direction of the practitioner D and the orientation of the body of the practitioner D. The learning function 217 is configured to learn that the possibility for the occurrence of an abnormality changes, on the basis of such moving directions and speeds of the medical devices and the medical providers. Through this learning process, the learning function 217 is able to generate the first trained model 91 taking into account the occurrences of abnormalities caused by the moving of an object or a human being.

Further, in the present embodiment, on the basis of the learning-purpose non-image data with an abnormality 1072 and the learning-purpose non-image data with no abnormalities 2072, the learning function 217 is configured to learn that the possibility for the occurrence of an abnormality changes depending on: the manipulation information related to the manipulation; the patient information related to the patient P; the practitioner information related to the practitioners D who perform the manipulation; the device information related to the devices used for the manipulation; and the medical institution information related to the medical institution where the examination room R1 is provided. For example, the learning function 217 is configured to learn the situations where the possibility for the occurrence of an abnormality becomes higher or lower, depending on the degrees of proficiency of the practitioners D and the time of the day when the manipulation is performed.

Further, on the basis of the learning-purpose non-image data with an abnormality 1072 and the learning-purpose non-image data with no abnormalities 2072, the learning function 217 is configured to learn a relationship between the position information of the movable mechanisms included in the X-ray diagnosis apparatus 10 in the blind spots of the image taking device 30 that are not rendered in the examination room videos with an abnormality 1071 or the examination room videos with no abnormalities 2071 and how high the possibility is for the occurrence of an abnormality.

The learning function 217 is configured to save the generated first trained model 91 into the memory 24.

Further, the learning function 217 is configured to generate the second trained model 92 by learning the correspondence relationship between the objects rendered in the examination room videos and the names of the objects; and the correspondence relationship between the risk regions included in the examination room videos and phrases each explaining an abnormality having a high possibility of occurring in a risk region included in any of the examination room videos.

Figure 5:
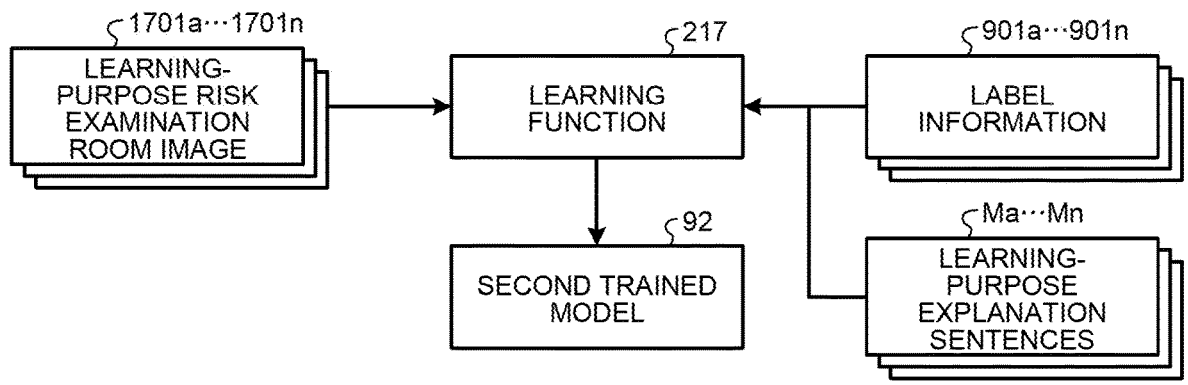
FIG. 5 is a chart illustrating an example of a method for generating a second trained model according to the first embodiment.

FIG. 5 is a chart illustrating an example of a method for generating the second trained model 92 according to the present embodiment. As illustrated in FIG. 5, the learning function 217 generates the second trained model 92 by learning a plurality of learning-purpose risk examination room images 1701a to 1701n, label information 901a to 901n, and a plurality of learning-purpose explanation sentences Ma to Mn.

Each of the plurality learning-purpose risk examination room images 1701a to 1701n is images in which the risk image 801 is superimposed on a frame rendering a situation having a high possibility for the occurrence of an abnormality. In the following sections, when not being individually distinguished from one another, the learning-purpose risk examination room images 1701a to 1701n may simply be referred to as a learning-purpose risk examination room image 1701.

Each pieces of label information 901a to 901n is information keeping an image region rendering an object in the learning-purpose risk examination room image 1701 in correspondence with the name of the object.

Each of the plurality of learning-purpose explanation sentences Ma to Mn is a sentence explaining an abnormality having a high possibility of occurring in the risk region presented in the risk image 801 in the learning-purpose risk examination room image 1701.

The sources from which the plurality of learning-purpose risk examination room images 1701a to 1701n, the plurality of label information 901a to 901n, and the plurality of learning-purpose explanation sentences Ma to Mn are obtained are not particularly limited. Further, the method for generating the second trained model 92 described above is merely an example. Besides the method described above, the learning function 217 is able to use any publicly-known method for learning natural sentences. The learning function 217 is configured to save the generated second trained model 92 into the memory 24.

Next, the following will explain a flow in an abnormality detecting process performed by the X-ray diagnosis apparatus 10 included in the system S according to the present embodiment structured as described above.

Figure 6:
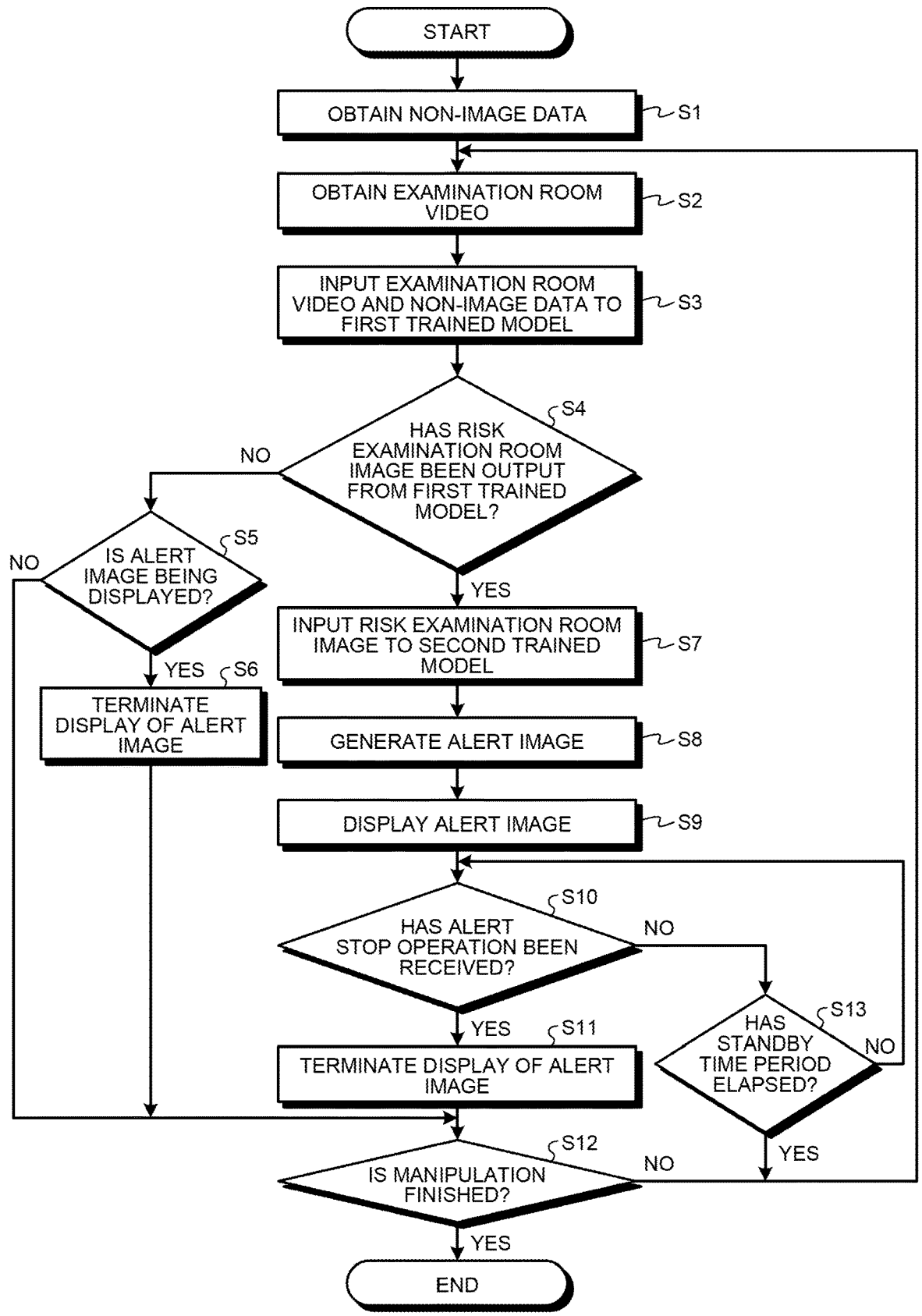
FIG. 6 is a flowchart illustrating an example of a flow in an abnormality detecting process according to the first embodiment.

FIG. 6 is a flowchart illustrating an example of the flow in the abnormality detecting process according to the present embodiment. The process illustrated in FIG. 6 starts when, for example, the controlling function 216 starts an image taking process on the patient P. Further, it is assumed that, prior to the start of the flowchart, the first trained model 91 and the second trained model 92 have been generated and saved in the memory 24.

To begin with, the obtaining function 211 obtains the non-image data 72 from an external device, the input interface 22, or the like (S1).

Further, the obtaining function 211 obtains the examination room video 71 capturing the inside of the examination room R1, from the image taking device 30 (S2).

Subsequently, the detecting function 212 inputs the examination room video 71 and the non-image data 72 obtained by the obtaining function 211 to the first trained model 91 (S3). As for the examination room video 71, the detecting function 212 sequentially inputs the frames included in the examination room video 71 in a time series, to the first trained model 91.

After that, the detecting function 212 judges whether or not a risk examination room image 701 has been output from the first trained model 91 (S4). When no risk examination room image 701 has been output from the first trained model 91, the examination room video 71 includes no risk region.

Accordingly, when having determined that no risk examination room image 701 has been output from the first trained model 91 (S4: No), the detecting function 212 determines that there is no abnormality having a high possibility of occurring in the examination room R1.

In that situation, the detecting function 212 notifies the alerting function 214 of the determination result indicating that there is no abnormality having a high possibility of occurring in the examination room R1. When an alert image 702 is already being displayed at this point in time (S5: Yes), the alerting function 214 terminates the display of the alert image 702 (S6). After that, the process proceeds to S12.

Also when no alert image 702 is being displayed (S5: No), the alerting function 214 proceeds to S12.

On the contrary, when having determined that a risk examination room image 701 has been output from the first trained model 91 (S4: Yes), the detecting function 212 sends the risk examination room image 701 having been output, to the explanation sentence generating function 213.

Subsequently, the explanation sentence generating function 213 inputs the risk examination room image 701 to the second trained model 92 (S7). The second trained model 92 generates an explanation sentence M explaining the "situation in which an abnormality is about to occur" rendered in the risk region presented in the risk image 801 within the risk examination room image 701.

After that, the explanation sentence generating function 213 generates the alert image 702 by adding the explanation sentence M to the risk examination room image 701 (S8). The explanation sentence generating function 213 sends the generated alert image 702 to the alerting function 214.

Further, the alerting function 214 causes the display devices 23a and 23b to display the alert image 702 generated by the explanation sentence generating function 213 (S9). Also, by controlling a speaker (not illustrated) or the like, the alerting function 214 may output the explanation sentence M via audio and/or may output an alert sound.

Subsequently, the receiving function 215 judges whether or not an alert stop operation being input by the operator has been received (S10). When having determined that an alert stop operation has been received (S10: Yes), the receiving function 215 notifies the alerting function 214 of the receipt of the alert stop operation. In that situation, the alerting function 214 terminates the display of the alert image 702 (S11). Also, when the explanation sentence M has been output via audio and/or the alert sound has been output, the alerting function 214 stops these outputs.

Subsequently, the receiving function 215 judges whether or not a manipulation finish operation being input by the operator has been received (S12). The manipulation finish operation is, for example, an operation to finish the image taking process. When the receiving function 215 determines that no manipulation finish operation has been received (S12: No), the process returns to S2 where the obtaining function 211 obtains a new examination room video 71.

On the contrary, at S10, when it is determined that no alert stop operation has been received (S10: No), the receiving function 215 judges whether or not a standby time period has elapsed (S13). Although the length of the standby time period is not particularly limited, the time period is, for example, long enough for the medical providers in the examination room R1 to solve the cause of the occurrence of the abnormality on the basis of the alert image 702. The standby time period may be determined in accordance with details of the abnormality determined to have a high possibility of occurring by the detecting function 212 or may be a time period of a fixed length.

While it is determined that the standby time period has not elapsed (S13: No), the receiving function 215 repeatedly performs the processes at S10 and S13, until it is determined that an alert stop operation has been received.

On the contrary, when the receiving function 215 determines that the standby time period has elapsed (S13: Yes), the process returns to S2 where the obtaining function 211 obtains a new examination room video 71. After that, the processes at S2 through S4 are performed. When the detecting function 212 determines that no risk examination room image 701 has been output from the first trained model 91, the alert image 702 displayed at S9 is terminated due to the processes at S5 and S6. In other words, even though the operator does not perform the alert stop operation, the display of the alert image 702 is terminated when the examination room videos 71 that are sequentially obtained by the X-ray diagnosis apparatus 10 no longer include any risk region. The process at S13 of judging whether or not the standby time period has elapsed may be performed by the obtaining function 211.

Further, when it is determined at S12 that the receiving function 215 has received a manipulation finish operation (S12: Yes), the process in the present flowchart ends.

Although this flowchart illustrates the example in which, after obtaining the non-image data 72 at the beginning of the process, the X-ray diagnosis apparatus 10 performs the abnormality detecting process by using the same non-image data 72. However, another arrangement is also acceptable in which non-image data 72 is newly obtained during the manipulation.

As explained above, the X-ray diagnosis apparatus 10 according to the present embodiment is configured to detect the situation having a high possibility for the occurrence of an abnormality in the examination room R1, on the basis of the examination room video 71 capturing the examination room R1 in which the manipulation is being performed on the patient P and the first trained model 91. Consequently, by using the X-ray diagnosis apparatus 10 according to the present embodiment, it is possible to detect, prior to the occurrence, the abnormality having a possibility of occurring in the examination room R1, by detecting the abnormality having the high possibility of occurring soon from the examination room video 71.

Further, by detecting the situation having a high possibility for the occurrence of an abnormality according to one or both of the moving speed and the moving direction of one of the objects and the human beings rendered in the examination room video 71, the X-ray diagnosis apparatus 10 according to the present embodiment is able to detect the abnormality caused by moving of an object or a human being, with a high level of precision.

Further, the first trained model 91 according to the present embodiment is configured to indicate the correspondence relationship between: the plurality of examination room videos with an abnormality 1071a to 1071n capturing the examination room R1; and the risk region information 802a to 802n having a high possibility for the occurrence of an abnormality in the plurality of examination room videos with an abnormality 1071a to 1071n. By inputting the examination room video 71 to the first trained model 91, the X-ray diagnosis apparatus 10 according to the present embodiment is able to detect the risk region that is an image region having a high possibility for the occurrence of an abnormality in the examination room video 71.

Further, the X-ray diagnosis apparatus 10 according to the present embodiment is configured to obtain the non-image data related to at least one of the manipulation, the patient P, and the examination room R1. Further, the first trained model 91 is configured to indicate the correspondence relationship among: the plurality of images capturing the examination room R1 (the plurality of examination room videos with an abnormality 1071a to 1071n and the plurality of examination room videos with no abnormalities 2071a to 2071n); the non-image data (the learning-purpose non-image data with an abnormality 1072a to 1072n and learning-purpose non-image data with no abnormalities 2072a to 2072n); and abnormalities having a high possibility of occurring in the examination room R1. Consequently, by using the X-ray diagnosis apparatus 10 according to the present embodiment, it is possible to detect the situation having a high possibility for the occurrence of an abnormality, while taking into account the information that is not rendered in the examination room video 71.

Further, when detecting that there is a high possibility for the occurrence of an abnormality, the X-ray diagnosis apparatus 10 according to the present embodiment is configured to alert about the high possibility for the occurrence of the abnormality. Accordingly, prior to the occurrence of the abnormality, the X-ray diagnosis apparatus 10 is able to help the medical providers and the like in the examination room R1 or the control room R2 understand that there is a high possibility for the occurrence of an abnormality.

Further, the non-image data 72 according to the present embodiment includes at least one of the following: the manipulation information related to the manipulation; the patient information related to the patient P; the practitioner information related to the practitioners D who perform the manipulation; the device information related to the devices used for the manipulation; and the medical institution information related to the medical institution where the examination room R1 is provided. The probability for the occurrence of an abnormality fluctuates depending on the type of the manipulation, the time of the day when the manipulation is performed, the devices such as various machines used for the manipulation, the seriousness of symptoms of the patient P, and/or the level of proficiency of the practitioners D. Consequently, by using these non-image data 72 for the detection, the X-ray diagnosis apparatus 10 according to the present embodiment is able to detect, with a high level of precision, the situation having a high possibility for the occurrence of an abnormality in the examination room R1.

Further, the X-ray diagnosis apparatus 10 according to the present embodiment is configured to generate the explanation sentence M explaining the abnormality having the high possibility of occurring in the detected risk region and issues the alert using the explanation sentence M. Accordingly, the medical providers and the like in the examination room R1 or the control room R2 are able to easily understand details of the abnormality having the high possibility of occurring.

Further, the X-ray diagnosis apparatus 10 according to the present embodiment is configured to generate the first trained model 91, by learning the relationship between: the abnormality pre-occurrence image capturing the space at the time prior to the occurrence of the abnormality during the manipulation; and the abnormality pre-occurrence image region rendering the location of the occurrence of abnormality in the abnormality pre-occurrence image. Consequently, by using the X-ray diagnosis apparatus 10 according to the present embodiment, it is possible to generate the first trained model 91 capable of detecting the situation prior to the occurrence of the abnormality, from the examination room video 71.

Further, the first trained model 91 and the second trained model 92 according to the present embodiment include "auto-learning models" configured to further update internal algorithms of the first trained model 91 and the second trained model 92, by obtaining user feedback on one of the risk examination room image 701 and the alert image 702 output by the X-ray diagnosis apparatus 10.

Furthermore, the first trained model 91 and the second trained model 92 may each be constructed by using an integrated circuit such as an ASIC, an FPGA, or the like. Further, the first correspondence information and the second correspondence information do not necessarily have to be trained models. For instance, the first correspondence information and the second correspondence information may each be a mathematical expression model, a lookup table, a database, or the like.

Second Embodiment

The x-ray diagnosis apparatus 10 of the present embodiment uses a different first trained model 91 depending on a protocol of examination.

The system S of the present embodiment includes the x-ray diagnosis apparatus 10 and the image taking device 30, similar to that of the first embodiment. The image taking device 30 of the present embodiment has the same function as that of the first embodiment has. The x-ray diagnosis apparatus 10 of the present embodiment has the same function as that of the first embodiment has. The x-ray diagnosis apparatus 10 is an example of a medical information processing apparatus according to the present embodiment.

The processing circuitry 21 of the x-ray diagnosis apparatus 10 of the present embodiment includes, similar to that of the first embodiment, the obtaining function 211, the detecting function 212, the explanation sentence generating function 213, the alerting function 214, the receiving function 215, the controlling function 216, and the learning function 217. The obtaining function 211, the explanation sentence generating function 213, the alerting function 214, the receiving function 215, and the controlling function 216 have the same functions as those of the first embodiment.

The x-ray diagnosis apparatus 10 of the present embodiment also includes a plurality of first trained models 91 each being trained for a respective one of the types of non-image data 1072 and 2072.

More particularly, the non-image data 72, 1072, and 2072 include a type of protocol, which is one of manipulation information related to a manipulation. The type of protocol is hereinafter simply referred to as "protocol". The type of protocol is an example of type of the non-image data.

As described in the first embodiment, the protocol is a processing procedure determined for each treated site. In the present embodiment, for example, a processing procedure determined for a treated site included in an examination executed by the x-ray diagnosis apparatus 10 is referred to as a protocol of an examination. In other words, the non-image data 72, 1072, and 2072 of the present embodiment include a protocol of an examination executed by the x-ray diagnosis apparatus 10.

The x-ray diagnosis apparatus 10 of the present embodiment also includes a plurality of first trained models 91 each been trained for a respective one of protocols of examinations included in the non-image data 1072 and 2072. The plurality of first trained models 91 is stored in the memory 24, each being association with the protocol of the examination, for example.

The detecting function 212 of the present embodiment detects, in addition to the function of the first embodiment, a risk region by inputting the examination room video 71 and the non-image data 72 obtained by the obtaining function 211 to a first trained model corresponding to the non-image data 72 obtained by the obtaining function 211, the risk region being an image region having a high possibility for an occurrence of an abnormality in the image obtained. More particularly, the detecting function 212 inputs the examination room video 71 and the non-image data 72 obtained by the obtaining function 211 to a first trained model corresponding to the protocol of the examination included in the non-image data 72 obtained by the obtaining function 211.

The examination room video 71 is an example of image obtained by the obtaining function 211. The non-image data 72 is an example of non-image information.

In other words, the detecting function 212 selects, among the plurality of first trained models 91 stored in the memory 24, a first trained model 91 associated with the same protocol as the protocol of the examination that is included in the non-image data 72 obtained by the obtaining function 211. The detecting function 212 then inputs the examination room video 71 and the non-image data 72 obtained by the obtaining function 211 to the selected first trained model 91.

Each protocol of examination has different standing positions of the practitioners D and the medical staff W in the examination room R1. Moreover, each protocol of examination has different positions and timings of movement of the C-arm 15 or the tabletop 14.

Due to this, the x-ray diagnosis apparatus 10 of the present embodiment can detect an occurrence of an abnormality in the examination room R1 with a high level of precision by using a first trained model 91 corresponding to a protocol of examination.

The learning function 217 of the present embodiment generates a first trained model 91 for each protocol of examination, in addition to the function of the first embodiment. For example, the learning function 217 obtains, for each protocol of examination, the plurality of examination room videos with abnormalities 1071a to 1071n, the plurality of examination room videos with no abnormalities 2071a to 2071n, the learning-purpose non-image data with abnormalities 1072a to 1072n, and the plurality of learning-purpose non-images with no abnormalities 2072a to 2072n as learning data. The Learning function 217 also obtains the risk region information 802a to 802n as training data. The learning function 217 generates the first trained models 91 by performing deep learning using a CNN, an RNN, or the like, on the basis of the learning data and training data described above.

Although, in the present embodiment, the first trained model 91 is generated for each protocol of examination, which is one of information included in the non-image data 1072 and 2072, the first trained model 91 may be generated for each information other than the protocol of examination.

First Modification Example

In the first and second embodiments above, the X-ray diagnosis apparatus 10 serves as an example of the medical information processing apparatus; however, the medical information processing apparatus may be an information processing apparatus different from the X-ray diagnosis apparatus 10. For example, the medical information processing apparatus may be a Personal Computer (PC), a server apparatus, or the like provided on the outside of the examination room R1. For example, the Personal Computer (PC), the server apparatus, or the like is connected to the X-ray diagnosis apparatus 10 via an intra-hospital network, or the like.

Further, the medical information processing apparatus may be any of other types of modalities such as an X-ray Computed Tomography (CT) apparatus, a Magnetic Resonance Imaging (MRI) apparatus, an ultrasound diagnosis apparatus, a Positron Emission Tomography (PET) apparatus, or a Single Photon Emission Computed Tomography (SPECT) apparatus.

Second Modification Example

Further, in the above first and second embodiments, the examination room R1 used for the catheter treatment serves as an example of the space; however, possible examples of the space from which abnormalities are detected are not limited to this example. For instance, a surgery room or the interior of an ambulance may be used as an example of the space.

Third Modification Example

Further, in the above first and second examples, the learning function 217 is configured to generate the first trained model 91 and the second trained model 92; however, another information processing apparatus may be configured to generate the first trained model 91 and the second trained model 92. The X-ray diagnosis apparatus 10 may be configured to obtain the first trained model 91 and the second trained model 92 from the other information processing apparatus and to save the obtained models into the memory 24.

Fourth Modification Example

Further, besides the image taking device 30, the system S may include various types of sensors provided in the examination room R1. For example, the system S may include a three-dimensional (3D) sensor capable of measuring distances to objects. When this configuration is used, the detecting function 212 of the X-ray diagnosis apparatus 10 is further configured to detect a situation having a high possibility for the occurrence of an abnormality in the examination room R1, on the basis of the distances to the objects measured by the 3D sensor. When this configuration is used, the learning function 217 is further configured to generate the first trained model 91 by using the distances to the objects measured by the 3D sensor as learning data.

Fifth Modification Example

Further, the system S may include position sensors attached to the medical providers in the examination room R1. The position sensors may be, for example, wearable devices each configured to transmit the position of the medical provider.

In the present modification example, the obtaining function 211 is configured to obtain position information of each of the plurality of medical providers during the manipulation. Further, in that situation, the practitioner information included in the non-image data 72 includes the position information of the practitioners D in the examination room R1. Alternatively, the non-image data 72 may include the position information of not only the practitioners D, but all the medical providers in the examination room R1.

In the present modification example, the detecting function 212 is further configured to detect the situation having a high possibility for the occurrence of an abnormality in the examination room R1, on the basis of the position information of the practitioners D or the other medical providers during the manipulation. According to the present modification example, the X-ray diagnosis apparatus 10 is able to, for example, detect the situation having the high possibility for the occurrence of the abnormality in the examination room R1, by taking into account the position information of the practitioners D or the other medical providers in the blind spots of the image taking device 30 that are not rendered in the examination room video 71. For example, the X-ray diagnosis apparatus 10 is able to detect, prior to the occurrence, medical providers coming into contact with each other, a medical provider coming into contact with a medical device, or the like, in a position that is not rendered in the examination room video 71.

Further, when this configuration is used, the learning function 217 is further configured to generate the first trained model 91 by using the obtained positions of the medical providers as learning data.

Sixth Modification Example

In the above first and second embodiments, the image taking device 30 is configured to take the examination room video 71; however, the image taking device 30 may be configured to take one or more still images. When this configuration is used, on the basis of the first trained model 91 and at least an image capturing the examination room R1, the detecting function 212 is configured to detect a risk region in the still image. Further, in that situation, the learning function 217 is configured to also use the still image, instead of the video, in the process of generating the first trained model 91. Further, when the still image is used as learning data, the first trained model 91 may be generated by a CNN.

Seventh Modification Example

In the above first and second embodiments, the first trained model 91 is saved in the memory 24; however, the first trained model 91 may be incorporated in the detecting function 212. In addition, the second trained model 92 may also be incorporated in the explanation sentence generating function 213.

Eighth Modification Example

In the above first and second embodiments, the learning function 217 is configured to perform the supervised learning process using the risk region information 802, when generating the first trained model 91; however, possible learning methods are not limited to this example. For instance, a semi-supervised learning process may be used. Further, the learning function 217 may be configured to use a semi-supervised learning process, also for generating the second trained model 92.

Ninth Modification Example

Further, in the above first and second embodiments, the learning function 217 is configured to use the risk region information 802 as the training data; however, possible examples of the training data are not limited to this example. For instance, the learning function 217 may use, as training data, abnormality region information with which it is possible to identify an abnormality region rendering the situation in which an abnormality has actually occurred, instead of the situation immediately prior to the occurrence of the abnormality. For example, the abnormality region information may be information with which it is possible to identify a frame rendering the abnormality included in an examination room video with an abnormality 1071 and the abnormality region that is an image region rendering the abnormality in the frame. When this configuration is used, the learning function 217 is configured to learn the image region rendering the same object as that in the abnormality region, in the frame immediately preceding the frame rendering the abnormality identified by the abnormality region information, as a risk region having a high possibility for the occurrence of the abnormality.

Tenth Modification Example

The non-image data 72, 1072, and 2072 may include operational information of the C-arm 15 in addition to the information exemplified above in the first and second embodiments.

The operational information of the C-arm 15 includes, in a case of manual control, for example, a moving direction and a moving speed. The operational information of the C-arm 15 includes, in a case of sequence operation, a moving range of the C-arm 15. The movable mechanism of the present modification example includes the C-arm 15, at least. The manual control is a control in which the practitioner D manually operates the C-arm 15 through control of an operation unit of the X-ray diagnosis apparatus 10. The sequence operation is an operation in which the C-arm 15 automatically operates in accordance with an input sequence.

The X-ray diagnosis apparatus 10 of the present modification example detects a situation having a high possibility for an occurrence of an abnormality on the basis of the operational information of the C-arm 15. Due to this, the X-ray diagnosis apparatus 10 of the present modification example can estimate an occurrence of interference between the C-arm 15 and the practitioner D or the medical staff W with a high level of precision.

Eleventh Modification Example

The non-image data 72, 1072, and 2072 may include voice data related to interactions between the examination room R1 and the control room R2, in addition to the information exemplified above in the first and second embodiments.

Voice data is transferred between the examination room R1 and the control room R2 via a microphone and a speaker provided in each of the examination room R1 and the control room R2. The non-image data 22, 1072, and 2072 of the present modification example includes the voice data.

When, for example, the supervisor in the control room R2 makes an oral instruction for the practitioner D in the examination room R1, the voice data includes contents of the instruction. If the practitioner D performs operation inconsistent with the instruction due to an error in hearing, etc., inconsistence occurs between the situation of the examination room R1 included in the examination room video 71 and the contents of the instruction included in the voice data. Due to this, the x-ray diagnosis apparatus 10 of the present modification example can detect information having a high possibility for an occurrence of an abnormality in the examination room R1 with a high level of precision by using the non-image data 72 including voice data.

The voice data included in the non-image data 72, 1072, and 2072 is not limited to voice data actually sent or received to/from the examination room R1 or the control room R2. The voice data may be, for example, voice each collected by the microphone provided in either the examination room R1 or the control room R2.

Twelfth Modification Example

Although, in the first and second embodiments above, the image taking device 30 is for example installed on the ceiling of the examination room R1, the installation position of the image taking device 30 is not limited thereto. The image taking device 30 may, for example, image the examination room R1 from outside of the examination room R1. If the control room R2 and the examination room R1 are separated from each other by a transparent material, such as glass, the image taking device 30 may be installed on the control room R2. In this situation, the image taking device 30 images the inside of the examination room R1 from the control room R2. In addition, the image taking device 30 may image the inside of the control room R2.

The image taking device 30 is arranged such that at least part of or the whole of the movable mechanism is within a field of view of the image taking device 30, regardless of the position of the movable mechanism. The image taking device 30 is more preferably arranged such that at least part of or the whole of the C-arm 15 included in the movable mechanism is within the field of view of the image taking device 30, regardless of the position of the movable mechanism.

Thirteenth Modification Example

The x-ray diagnosis apparatus 10 may be configured as a biplane including the C-arm 15 and an Ω arm. The movable mechanism of the present modification example includes at least the C-arm 15 and the Ω arm. In addition, the movable mechanism may include the tabletop 14.

The image taking device 30 is preferably arranged such that at least part of or the whole of the C-arm 15 and the Ω arm included in the movable mechanism are within the field of view of the image taking device 30, regardless of the position of the movable mechanism.

According to at least one aspect of the embodiments described above, it is possible to detect, prior to the occurrence, the abnormality having a high possibility of occurring in the examination room R1.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising processing circuitry configured to:

obtain an examination room image capturing an inside of the examination room in which a manipulation is being performed on an examined subject and non-image information related to at least one of the manipulation, the examined subject, or the inside of the examination room;

generate a risk image superimposed on a risk region by inputting the obtained examination room image and the obtained non-image information to a first trained model, the risk region being a region having a high possibility for an occurrence of an abnormality in the examination room indicated by the examination room image;

generate a sentence by inputting the examination room image having the risk image superimposed on the risk region to a second trained model, wherein the second trained model is a trained model that has been trained with a correspondence relationship between a plurality of risk regions in two or more examination room images capturing the inside of the examination room and the sentence explaining a situation in which the abnormality is likely to occur in the risk region indicated by the risk image based on the second trained module;

and output on a display (i) the examination room image having the risk image superimposed on the risk region and (ii) the sentence.

2. The medical information processing apparatus according to claim 1, wherein the obtained examination room image is a video, and the processing circuitry is configured to output the sentence explaining the situation according to one or both of a moving speed and a moving direction of one of an object or a human being rendered in the obtained video.

3. The medical information processing apparatus according to claim 1, wherein the first trained model is one of two or more trained models each having been trained with a correspondence relationship between two or more examination room images capturing the examination room and image regions each having a high possibility for an occurrence of an abnormality in the two or more examination room images, the two or more trained models each being trained for a respective one of two or more types of the non-image information, and the processing circuitry is configured to detect a risk region that is an image region having a high possibility for an occurrence of an abnormality in the obtained examination room image, by inputting the obtained examination room image to the first trained model corresponding to the obtained non-image information.

4. The medical information processing apparatus according to claim 1, wherein the first trained model is a trained model that has been trained with a correspondence relationship between two or more examination room images capturing the examination room and image regions each having a high possibility for an occurrence of an abnormality in the two or more examination room images, and the processing circuitry is configured to detect a risk region that is an image region having a high possibility for an occurrence of an abnormality in the obtained examination room image, by inputting the obtained examination room image to the first trained model.

5. The medical information processing apparatus according to claim 1, wherein the non-image information includes at least one of the following: manipulation information related to the manipulation; examined subject information related to the examined subject, practitioner information related to a practitioner who performs the manipulation; device information related to a device used for the manipulation; and medical institution information related to a medical institution where the examination room is provided.

6. The medical information processing apparatus according to claim 1, wherein the second trained model is a trained model that has been trained with a correspondence relationship between a plurality of risk regions in two or more examination room images capturing the inside of the examination room and the sentence explaining abnormalities having a high possibility of occurring in the plurality of risk regions, and the processing circuitry outputs the sentence explaining the situation based on the second trained model.

7. The medical information processing apparatus according to claim 4, wherein the processing circuitry is configured to generate the first trained model by learning a correspondence relationship between abnormality pre-occurrence image capturing the examination room at a time prior to the occurrence of the abnormality during the manipulation and abnormality pre-occurrence image regions rendering locations of the occurrence of the abnormality within the abnormality pre-occurrence image.

8. A system comprising an image taking device and a medical information processing apparatus, wherein the image taking device is configured to image an examination room in which a manipulation is being performed on an examined subject, the medical information processing apparatus includes processing circuitry, and the processing circuitry is configured to:

obtain an examination room image captured by the image taking device and non-image information related to at least one of the manipulation, the examined subject, or an inside of the examination room;

generate a risk image superimposed on a risk region by inputting the obtained examination room image and the obtained non-image information to a first trained model, the risk region being a region having a high possibility for an occurrence of an abnormality in the examination room indicated by the examination room image;

generate a sentence by inputting the examination room image having the risk image superimposed on the risk region to a second trained model, wherein the second trained model is a trained model that has been trained with a correspondence relationship between a plurality of risk regions in two or more examination room images capturing the inside of the examination room and the sentence explaining a situation in which the abnormality is likely to occur in the risk region indicated by the risk image based on the second trained module; and output on a display (i) the examination room image having the risk image superimposed on the risk region and (ii) the sentence.

9. The system according to claim 8, wherein the obtained examination room image is a video, and the processing circuitry is configured to output the sentence explaining the situation according to one or both of a moving speed and a moving direction of one of an object or a human being rendered in the obtained video.

10. The system according to claim 8, wherein the first trained model is one of two or more trained models each having been trained with a correspondence relationship between two or more examination room images capturing the examination room and image regions each having a high possibility for an occurrence of an abnormality in the two or more examination room images, the two or more trained models being each trained for a respective one of two or more types of the non-image information, and the processing circuitry is configured to detect a risk region that is an image region having a high possibility for an occurrence of an abnormality in the obtained examination room image, by inputting the obtained examination room image to the first trained model corresponding to the obtained non-image information.

11. The system according to claim 8, wherein the first trained model is a trained model that has been trained with a correspondence relationship between two or more examination room images capturing the examination room and image regions each having a high possibility for an occurrence of an abnormality in the two or more examination room images, and the processing circuitry is configured to detect a risk region that is an image region having a high possibility for an occurrence of an abnormality in the obtained examination room image data, by inputting the obtained examination room image to the first trained model.

12. The system according to claim 8, wherein the non-image information includes at least one of the following: manipulation information related to the manipulation; examined subject information related to the examined subject, practitioner information related to a practitioner who performs the manipulation; device information related to a device used for the manipulation; and medical institution information related to a medical institution where the examination room is provided.

13. The system according to claim 8, wherein the second trained model is a trained model that has been trained with a correspondence relationship between a plurality of risk regions in two or more examination room images capturing the inside of the examination room and the sentence explaining abnormalities having a high possibility of occurring in the plurality of risk regions, and the processing circuitry outputs the sentence explaining the situation based on the second trained model.

14. The system according to claim 11, wherein the processing circuitry generates the first trained model by learning a correspondence relationship between abnormality pre-occurrence image capturing the examination room at a time prior to the occurrence of the abnormality during the manipulation and abnormality pre-occurrence image regions rendering locations of the occurrence of the abnormality within the abnormality pre-occurrence image.

15. An X-ray diagnosis apparatus comprising processing circuitry configured to:

obtain an examination room image capturing an inside of the examination room in which a manipulation is being performed on an examined subject and non-image information related to at least one of the manipulation, the examined subject, or the inside of the examination room; generate a risk image superimposed on a risk region by inputting the obtained examination room image and the obtained non-image information to a first trained model, the risk region being a region having a high possibility for an occurrence of an abnormality in the examination room indicated by the examination room image;

generate a sentence by inputting the examination room image having the risk image superimposed on the risk region to a second trained model, wherein the second trained model is a trained model that has been trained with a correspondence relationship between a plurality of risk regions in two or more examination room images capturing the inside of the examination room and the sentence explaining a situation in which the abnormality is likely to occur in the risk region indicated by the risk image based on the second trained module;

and output on a display (i) the examination room image having the risk image superimposed on the risk region and (ii) the sentence.

16. The X-ray diagnosis apparatus according to claim 15, wherein the obtained examination room image is a video, and the processing circuitry is configured to output the sentence explaining the situation according to one or both of a moving speed and a moving direction of one of an object or a human being rendered in the obtained video.

17. The X-ray diagnosis apparatus according to claim 15, wherein the first trained model is a trained model that has been trained with a correspondence relationship between two or more examination room images capturing the examination room and image regions each having a high possibility for an occurrence of an abnormality in the two or more examination room images, and the processing circuitry is configured to detect a risk region that is an image region having the high possibility for the occurrence of the abnormality in the obtained examination room image, by inputting the obtained examination room image to the first trained model.

18. The X-ray diagnosis apparatus according to claim 15, wherein the first trained model is one of two or more trained models each having been trained with a correspondence relationship between two or more examination room images capturing the examination room and image regions each having a high possibility for an occurrence of an abnormality in the two or more examination room images, the two or more trained models each being trained for a respective one of two or more types of the non-image information, and the processing circuitry is configured to detect a risk region that is an image region having a high possibility for an occurrence of an abnormality in the obtained examination room image, by inputting the obtained examination room image to the first trained model corresponding to the obtained non-image information.

* * * * *